(12) United States Patent
Nakazawa et al.

(10) Patent No.: US 9,656,248 B2
(45) Date of Patent: May 23, 2017

(54) CATALYST FOR PRODUCING UNSATURATED ALDEHYDE AND/OR UNSATURATED CARBOXYLIC ACID, METHOD FOR PRODUCING SAME, AND METHOD FOR PRODUCING UNSATURATED ALDEHYDE AND/OR UNSATURATED CARBOXYLIC ACID

(71) Applicant: Nippon Kayaku Kabushiki Kaisha, Tokyo (JP)

(72) Inventors: Yuuta Nakazawa, Yamaguchi (JP); Yoshiko Shoya, Yamaguchi (JP); Masaki Nakahara, Yamaguchi (JP); Eiji Nishimura, Yamaguchi (JP); Kazuo Shiraishi, Gunma (JP); Tatsuhiko Kurakami, Yamaguchi (JP); Ryota Hiraoka, Yamaguchi (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/784,652

(22) PCT Filed: May 8, 2014

(86) PCT No.: PCT/JP2014/062390
§ 371 (c)(1),
(2) Date: Oct. 15, 2015

(87) PCT Pub. No.: WO2014/181839
PCT Pub. Date: Nov. 13, 2014

(65) Prior Publication Data
US 2016/0059218 A1    Mar. 3, 2016

(30) Foreign Application Priority Data
May 9, 2013  (JP) ................. 2013-099647

(51) Int. Cl.
| | | |
|---|---|---|
| C07C 45/35 | (2006.01) |
| C07C 47/22 | (2006.01) |
| C07C 57/04 | (2006.01) |
| B01J 23/843 | (2006.01) |
| B01J 23/887 | (2006.01) |
| B01J 37/04 | (2006.01) |
| B01J 23/88 | (2006.01) |
| B01J 35/08 | (2006.01) |
| C07C 51/25 | (2006.01) |
| B01J 23/00 | (2006.01) |
| B01J 35/02 | (2006.01) |
| B01J 37/00 | (2006.01) |

(52) U.S. Cl.
CPC ......... *B01J 23/8876* (2013.01); *B01J 23/002* (2013.01); *B01J 23/88* (2013.01); *B01J 35/023* (2013.01); *B01J 35/08* (2013.01); *B01J 37/0018* (2013.01); *B01J 37/04* (2013.01); *C07C 45/35* (2013.01); *C07C 51/252* (2013.01); *B01J 2523/00* (2013.01)

(58) Field of Classification Search
CPC ...... B01J 23/8876; B01J 23/88; B01J 23/002; C07C 45/35
See application file for complete search history.

(56) References Cited

U.S. PATENT DOCUMENTS

| | | | |
|---|---|---|---|
| 4,792,620 A * | 12/1988 | Paulik ................. | B01J 31/0231 560/232 |
| 4,916,103 A | 4/1990 | Martan et al. | |
| 5,929,275 A * | 7/1999 | Wada ..................... | B01J 23/002 502/306 |
| 6,028,220 A | 2/2000 | Wada et al. | |
| 6,383,976 B1 | 5/2002 | Arnold et al. | |
| 6,632,965 B1 | 10/2003 | Tanimoto et al. | |
| 7,005,542 B2 | 2/2006 | Yunoki | |
| 7,208,636 B2 | 4/2007 | Petzoldt et al. | |
| 7,414,008 B2 | 8/2008 | Yunoki | |

(Continued)

FOREIGN PATENT DOCUMENTS

| | | |
|---|---|---|
| CN | 1165055 A | 11/1997 |
| CN | 1210511 A | 3/1999 |

(Continued)

OTHER PUBLICATIONS

Norskov et al, Nature Chemistry, Towards the Computational Design of Solid Catalysts, 2009, 1, pp. 37-46.*
Japanese communication, with English translation, dated Feb. 16, 2016 in corresponding Japanese patent application No. 2015-515896.
International Search Report and Written Opinion mailed Jul. 15, 2014 in corresponding PCT application No. PCT/JP2014/062390.
Chinese communication, with English translation, dated Aug. 18, 2016 in corresponding Chinese patent application No. 201480025998.9.
European communication dated Nov. 29, 2016 in corresponding European patent application No. 14795050.5.

(Continued)

*Primary Examiner* — Paul A Zucker
(74) *Attorney, Agent, or Firm* — Nields, Lemack & Frame, LLC

(57) ABSTRACT

Provided is a catalyst having high activity and yield of a target product for producing an unsaturated aldehyde and/or an unsaturated carboxylic acid and further having high mechanical strength. The catalyst is a catalyst prepared by a method in which a catalyst formulation satisfies specified atomic ratios; and in the preparation thereof, a molybdenum component raw material is an ammonium molybdate, a solvent for dissolving the ammonium molybdate is water, a bismuth component raw material is bismuth nitrate, and a solvent for dissolving bismuth nitrate is a nitric acid aqueous solution, and the weight of water for dissolving the ammonium molybdate, the weight of the nitric acid aqueous solution for dissolving the bismuth nitrate, and the acid concentration of the nitric acid aqueous solution are satisfied with specified ranges, respectively.

5 Claims, No Drawings

(56) References Cited

U.S. PATENT DOCUMENTS

| | | | |
|---|---|---|---|
| 8,969,618 B2 | 3/2015 | Kurakami et al. | |
| 2002/0136678 A1 | 9/2002 | Tanimoto et al. | |
| 2003/0162998 A1 | 8/2003 | Yunoki | |
| 2005/0107641 A1 | 5/2005 | Petzoldt et al. | |
| 2006/0036111 A1 | 2/2006 | Yunoki | |
| 2006/0245992 A1* | 11/2006 | Tanimoto | B01J 8/0015 422/310 |
| 2007/0142223 A1 | 6/2007 | Petzoldt et al. | |
| 2013/0023699 A1 | 1/2013 | Macht et al. | |
| 2013/0310604 A1 | 11/2013 | Kurakami et al. | |

FOREIGN PATENT DOCUMENTS

| | | |
|---|---|---|
| CN | 1440834 A | 9/2003 |
| CN | 1162382 C | 8/2004 |
| CN | 1291781 C | 12/2006 |
| CN | 101690900 A | 4/2010 |
| CN | 102627537 A | 8/2012 |
| EP | 0456837 A1 | 11/1991 |
| JP | 61-137833 A | 6/1986 |
| JP | 01-168344 A | 7/1989 |
| JP | 10-028877 A | 2/1998 |
| JP | 10-168003 A | 6/1998 |
| JP | 2000-169149 A | 6/2000 |
| JP | 2003-146920 A | 5/2003 |
| JP | 2003-164763 A | 6/2003 |
| JP | 2004-516132 A | 6/2004 |
| JP | 2007-511565 A | 5/2007 |
| JP | 2007-175600 A | 7/2007 |
| JP | 2012-115825 A | 6/2012 |
| JP | 2012-176938 A | 9/2012 |
| KR | 1999-0077024 A | 10/1999 |
| WO | 2009/057463 A1 | 5/2009 |

OTHER PUBLICATIONS

Korean communication, with English translation, dated Jan. 18, 2017 in corresponding Korean patent application No. 10-2015-7028070.

Chinese communication, with English translation, dated Mar. 27, 2017 in corresponding Chinese patent application No. 201480025998.9.

* cited by examiner

CATALYST FOR PRODUCING UNSATURATED ALDEHYDE AND/OR UNSATURATED CARBOXYLIC ACID, METHOD FOR PRODUCING SAME, AND METHOD FOR PRODUCING UNSATURATED ALDEHYDE AND/OR UNSATURATED CARBOXYLIC ACID

TECHNICAL FIELD

The present invention relates to a complex metal oxide catalyst which is used on the occasion of subjecting an alkene to gas-phase oxidation with molecular oxygen or a molecular oxygen-containing gas in the presence of an oxidation catalyst to produce an unsaturated aldehyde and/or an unsaturated carboxylic acid each corresponding to the alkene, a method for producing the same, and a method for producing an unsaturated aldehyde and/or an unsaturated carboxylic acid.

BACKGROUND ART

With respect to catalysts for subjecting propylene to gas-phase catalytic oxidation with molecular oxygen to synthesize acrolein and acrylic acid, there have hitherto been made a large number of proposals, and in general, catalyst systems thereof are frequently dealt as the same system. Among those, a technology regarding an atomic ratio of iron and cobalt and nickel is described in Patent Document 1, and it is described that by allowing the atomic ratio of iron to cobalt and/or nickel to fall within a specified range, the activity and selectivity can be improved. Patent Document 2 discloses a technology of preparing plural catalysts in which while making an atomic ratio of iron to cobalt and/or nickel constant, an atomic ratio of cobalt relative to an atomic ratio of cobalt and nickel is changed, and filling them in two or more layers of reaction bands within a reaction vessel and using it. Patent Document 3 discloses a technology regarding an annular unsupported catalyst in which an atomic ratio of cobalt relative to an atomic ratio of molybdenum and an atomic ratio of cobalt relative to an atomic ratio of iron are set to specified values, respectively. Patent Document 4 discloses a technology regarding an iron raw material and discloses that by using iron molybdate as the raw material, a catalyst in a high yield can be produced. Patent Document 5 discloses a catalyst in which a part of a bismuth raw material is added to a dry powder containing other catalyst constituent elements. Patent Document 6 discloses a catalyst in which bismuth trioxide is used as a bismuth raw material. Patent Document 7 discloses a technology regarding an atomic ratio of bismuth to molybdenum, an atomic ratio of cobalt and/or nickel to molybdenum, an atomic ratio of iron to molybdenum, and an atomic ratio of an alkali metal to molybdenum and discloses a catalyst containing a specified crystal and not containing molybdenum trioxide. Patent Document 8 discloses a catalyst in which the range of a value A obtained by subtracting a value of 1.5 times of an atomic ratio of cobalt and an atomic ratio of iron from an atomic ratio of molybdenum is defined, and furthermore, an atomic ratio of bismuth to A and an atomic ratio of cobalt to iron are restricted; however, an atomic ratio of nickel is not investigated. In the light of the above, in the conventional technical ranges, there are a lot of cases where extensive investigations are made for the purpose of optimizing the atomic ratio of each of the elements to molybdenum; however, any inventions in which an atomic ratio of nickel relative to an atomic ratio of bismuth, an atomic ratio of nickel relative to an atomic ratio of an alkali metal component, and an atomic ratio of bismuth relative to an atomic ratio of an alkali metal component are investigated in detail, thereby clarifying effects thereof (activity, effective yield, and mechanical strength) have not been found yet.

BACKGROUND ART DOCUMENT

Patent Document

Patent Document 1: JP-A-2003-164763
Patent Document 2: JP-A-2003-146920
Patent Document 3: JP-T-2007-511565
Patent Document 4: JP-A-H1-168344
Patent Document 5: JP-T-2004-516132
Patent Document 6: JP-A-2007-175600
Patent Document 7: JP-A-2000-169149
Patent Document 8: US-A-2013/0023699

SUMMARY OF INVENTION

Problem that Invention is to Solve

A part of methods of subjecting an alkene to a partial oxidation reaction to produce an unsaturated aldehyde and/or an unsaturated carboxylic acid each corresponding to the alkene has been industrialized; however, a more improvement of catalytic performance is demanded. For example, on the occasion of intending to produce, from an alkene, a large quantity of an unsaturated aldehyde and/or an unsaturated carboxylic acid each corresponding to the alkene by using the same oxidation reaction vessel, a supply load of the raw material alkene relative to the unit catalyst volume increases, so that it becomes necessary to increase a reaction bath temperature. This results in an increase of the temperature within the catalyst layer, thereby bringing a lowering of catalytic activity and/or selectivity with time, so that there may be the case where a problem is caused from the viewpoint of long-term use. An improvement of the catalytic activity makes it possible to decrease the reaction bath temperature, to reduce a running cost, and to prolong the catalyst life; and an improvement of the yield of the target product makes it possible to largely reduce a production cost. In addition, even if a shaping method of the catalyst used for this reaction is tableting shaping, extrusion shaping, coating shaping, or any other method, in the case where the mechanical strength is low as a result, at the time of filling the catalyst into an oxidation reaction vessel, powdering of the catalyst and exfoliation of the catalytically active component are generated, thereby clogging the interior of the oxidation reaction vessel and generating an abnormal increase of pressure in the reaction pipe. In order that a catalyst may exhibit its intrinsic excellent activity and effective yield, a catalyst having high mechanical strength is needed. In order to produce such an excellent catalyst, in a step of searching an optimal atomic ratio and preparing a catalyst having a specified atomic ratio found consequently, the weight of a solvent relative to the weight of the raw materials, the solvent being used for dissolving the raw materials to form a target complex metal oxide, and also, in the case of adding an acid to the solvent for dissolution, a concentration of the acid are important factors, and thorough investigations are needed.

An object of the present invention is to provide an excellent catalyst having high activity and yield of a target product for advantageously producing an unsaturated aldehyde and/or an unsaturated carboxylic acid and further having high mechanical strength (sometimes also expressed as "high-performance catalyst").

Means for Solving Problem

In order to solve the foregoing object, the present inventors made extensive and intensive investigations. As a result, they have found knowledge that a complex metal oxide catalyst in which a catalyst formulation thereof satisfies specified atomic ratios and which is prepared by a method in which in preparing the catalyst, a molybdenum component raw material is an ammonium molybdate, a solvent for dissolving the ammonium molybdate is water, and a bismuth component raw material is bismuth nitrate, and a solvent for dissolving bismuth nitrate is a nitric acid aqueous solution, and the weight of the water, the weight of the nitric acid aqueous solution and the acid concentration of the nitric acid aqueous solution satisfy specified ranges, respectively, has excellent mechanical strength and high activity and/or gives a target product in a high yield, leading to accomplishment of the present invention.

Specifically, the present invention is concerned with the followings.
(1) A catalyst for producing an unsaturated aldehyde and/or an unsaturated carboxylic acid, comprising:
  a compound represented by the following formula (1),
  the catalyst being prepared by a method in which in a step of preparing the compound represented by the following formula (1), a molybdenum component raw material is composed of only ammonium molybdate, a weight of water for dissolving the ammonium molybdate is 8.5 times or less relative to a weight of molybdenum contained in the ammonium molybdate, and a bismuth component raw material is composed of only bismuth nitrate, a weight of a nitric acid aqueous solution for dissolving the bismuth nitrate is 2.3 times or more relative to a weight of bismuth contained in the bismuth nitrate, and a nitric acid concentration of the nitric acid aqueous solution for dissolving the bismuth nitrate is 10% by weight or more:

$$Mo_{12}Bi_aFe_bCo_cNi_dX_eY_fZ_gO_h \quad \text{Formula (1)}$$

(in the formula, X is at least one element selected from the group consisting of magnesium (Mg), calcium (Ca), manganese (Mn), copper (Cu), zinc (Zn), cerium (Ce) and samarium (Sm); Y is at least one element selected from the group consisting of boron (B), phosphorus (P), asthenic (As), antimony (Sb) and tungsten (W); Z is at least element selected from the group consisting of sodium (Na), potassium (K), rubidium (Rb) and cesium (Cs); a to g represent atomic ratios of the respective components; h is a numerical value determined by degrees of oxidations of the catalyst components; a=0.80 to 2.0, b=1 to 2.5; c=3 to 7; d=2 to 3.5; e=0 to 10; f=0 to 10; g=0.01 to 0.10; h is expressed by the numerical value satisfying oxidation states of other elements; d/a is 1.9 or more and 3.2 or less; d/g is 29 or more and 69 or less; and a/g is 18 or more and 35 or less.)
(2) The catalyst for producing an unsaturated aldehyde and/or an unsaturated carboxylic acid as set forth in (1), wherein e and f in the formula (1) are 0.
(3) The catalyst for producing an unsaturated aldehyde and/or an unsaturated carboxylic acid as set forth in (1) or (2), which is prepared by shaping a preliminarily calcined powder obtained by calcining a dry powder obtained by drying a slurry containing the component of the formula (1), at a temperature of 200° C. or higher and 600° C. or lower and again calcining the preliminarily calcined powder at a temperature of 200° C. or higher and 600° C. or lower.

(4) The catalyst for producing an unsaturated aldehyde and/or an unsaturated carboxylic acid as set forth in any one of (1) to (3), wherein a shaping method of a catalyst is a method of coating a catalytically active component on a spherical carrier, an average particle diameter of an obtained catalyst is 3.0 mm to 10.0 mm, and a portion of a weight of the catalytically active component occupying in the whole of the catalyst is 20 to 80% by weight.
(5) A method for producing a catalyst, which a production method of the catalyst for producing an unsaturated aldehyde and/or an unsaturated carboxylic acid as set forth in (1), wherein in a step of preparing the compound represented by the formula (1), a molybdenum component raw material is composed of only ammonium molybdate, a weight of water for dissolving the ammonium molybdate is controlled to 8.5 times or less relative to a weight of molybdenum contained in the ammonium molybdate, and a bismuth component raw material is composed of only bismuth nitrate, a weight of a nitric acid aqueous solution for dissolving the bismuth nitrate is controlled to 2.3 times or more relative to a weight of bismuth contained in the bismuth nitrate, and a nitric acid concentration of the nitric acid aqueous solution for dissolving the bismuth nitrate is controlled to 10% by weight or more.
(6) A method for producing an unsaturated aldehyde and/or an unsaturated carboxylic acid comprising using the catalyst as set forth in any one of (1) to (4).

Effects of Invention

According to the present invention, an excellent catalyst having high activity and/or yield of a target product for producing, from an alkene, an unsaturated aldehyde and/or an unsaturated carboxylic acid each being corresponding to the alkene and further having high mechanical strength can be obtained. In the case where the activity is higher, it is possible to decrease the reaction temperature, and thermal deterioration can be suppressed. According to this, it becomes possible to stably perform a long-term operation.

MODE FOR CARRYING OUT INVENTION

The catalyst of the present invention can be prepared through the following steps.
Step a): Preparation
In general, as for starting raw materials of respective elements constituting the catalyst, in the case of using an ammonium molybdate as the molybdenum component raw material, a high-performance catalyst is obtained. In particular, the ammonium molybdate includes plural kinds of compounds, such as ammonium dimolybdate, ammonium tetramolybdate, ammonium heptamolybdate, etc., and among those, the case of using ammonium heptamolybdate is the most preferred. In the case of using bismuth nitrate as the bismuth component raw material, a high-performance catalyst is obtained. As for raw materials of iron, cobalt, nickel, and other elements, oxides, or nitrates, carbonates, organic acid salts, hydroxides, and the like, each of which can become an oxide upon ignition, or mixtures thereof can be generally used. For example, the iron component raw material and the cobalt component raw material and/or the nickel component raw material are dissolved in a prescribed ratio in water and mixed under a condition at 10 to 80° C.; the mixture is mixed with an aqueous solution or slurry of the separately prepared molybdenum component raw material and Z component raw material under a condition at 20 to 90° C.; after heating and stirring the resulting mixture for about 1 hour under a condition at 20 to 90° C., an aqueous solution having the bismuth component raw material dissolved therein and optionally the X component raw material and the Y component raw material are added, thereby obtaining an aqueous solution or slurry containing the catalyst components. The both are hereinafter collectively called "liquid preparation (A)". Here, the liquid preparation (A) is not always required to contain all of the catalyst constituent elements, and a part of those elements or a part of the amounts thereof may be added in the sequent step or steps. In addition, on the occasion of preparing the liquid preparation (A), when the amount of water for dissolving each of the component raw materials, or in the case of adding an acid, such as sulfuric acid, nitric acid, hydrochloric acid, tartaric acid, acetic acid, etc., for the purpose of dissolution, the acid concentration in the aqueous solution sufficient for dissolving the raw materials is not suitable within the range of, for example, 5% by weight to 99% by weight, there may be the case where the form of the liquid preparation (A) becomes a clay-like lump, and this does not become an excellent catalyst. In particular, it is preferred that in dissolving the molybdenum component raw material, the molybdenum component raw material is composed of only an ammonium molybdate, and the weight of water for dissolving it is 8.5 times or less relative to the weight of molybdenum contained in the ammonium molybdate, whereas in dissolving the bismuth component raw material, the bismuth component raw material is composed of only bismuth nitrate, the weight of the nitric acid aqueous solution for dissolving it is 2.3 times or more relative to the weight of bismuth contained in the bismuth nitrate, and the nitric acid concentration of the nitric acid aqueous solution for dissolving the bismuth nitrate is 10% by weight or more. From the standpoint of obtaining an excellent catalyst, the form of the liquid preparation (A) obtained in such a way is preferably an aqueous solution or slurry. Here, as for constituent element ratios, the ratios of nickel and the alkali metal which largely influence the activity as well as bismuth that is one of the catalyst main components are important, and it is preferred that d/a that is a ratio of nickel to bismuth is 1.9 or more and 3.2 or less, d/g that is a ratio of nickel to the alkali metal is 29 or more and 69 or less, and a/g that is a ratio of bismuth to the alkali metal is 18 or more and 35 or less. Thus, the resultant becomes an excellent catalyst having high activity and/or yield of a target product and further having high mechanical strength.

Step b): Drying

Subsequently, the liquid preparation (A) obtained above is dried to form a dry powder. The drying method is not particularly limited so long as it is a method capable of completely drying the liquid preparation (A); however, examples thereof include drum drying, freeze drying, spray drying, evaporation to dryness, and the like. Of these, spray drying in which the slurry can be dried into a powder or granule within a short period of time is especially preferred in the present invention. Although the drying temperature of spray drying varies depending upon the concentration of slurry, the liquid sending speed, or the like, it is approximately 70 to 150° C. in terms of a temperature at the outlet of a drying machine. In addition, it is preferred to perform drying such that an average particle diameter of the dry powder obtained on that occasion is 10 to 700 μm. There is thus obtained a dry powder (B).

Step c): Preliminary Calcination

When the obtained dry powder (B) is calcined under air circulation at 200° C. to 600° C., and preferably 300° C. to 600° C., shaping properties, mechanical strength, and catalytic performance of the resulting catalyst tend to be improved. A calcination time is preferably 1 hour to 12 hours. There is thus obtained a preliminarily calcined powder (C).

Step d): Shaping

Although the shaping method is not particularly limited, on the occasion of shaping in a cylindrical or annular form, a method using a tablet shaping machine, an extrusion shaping machine, or the like is preferred. The case of shaping in a spherical form is more preferred, and the preliminarily calcined powder (C) may be shaped in a spherical form by using a shaping machine; however, a method of supporting the preliminarily calcined powder (C) (including a shaping auxiliary agent and a strength improver, if desired) on a carrier, such as an inert ceramic, etc., is preferred. Here, as for the supporting method, a tumbling granulation method, a method using a centrifugal flow coating apparatus, a wash coating method, and the like are widely known, and the supporting method is not particularly limited so long as it is a method capable of uniformly supporting the preliminarily calcined powder (C) on the carrier. However, in the case of taking into account the production efficiency of the catalyst or the performance of the prepared catalyst, more preferably, a method in which using an apparatus having a flat or uneven disk in a bottom of a fixed cylindrical vessel, a carrier charged within the vessel is vigorously agitated by means of rotation motion and revolution motion of the disk itself by rotating the disk at a high speed, and the preliminarily calcined powder (C) and optionally a shaping auxiliary agent and/or a strength improver, and a pore forming agent are added thereto, thereby supporting the powder components on the carrier is preferred. It is to be noted that on the occasion of supporting, it is preferred to use a binder. Specific examples of the binder which may be used include water, ethanol, methanol, propanol, a polyhydric alcohol, polyvinyl alcohol that is a polymer-based binder, a silica sol aqueous solution that is an inorganic binder, and the like; ethanol, methanol, propanol, and a polyhydric alcohol are preferred; and a diol, such as ethylene glycol, etc., a triol, such as glycerin, etc., and the like are more preferred. By using an appropriate amount of a glycerin aqueous solution, the shaping properties become good, and a high-performance catalyst having high mechanical strength is obtained. Specifically, in the case of using an aqueous solution having a glycerin concentration of 5% by weight or more, a catalyst having an especially high performance is obtained. The use amount of such a binder is generally 2 to 80 parts by weight based on 100 parts by weight of the preliminarily calcined powder (C). As for the inert carrier, a carrier of about 2 to 8 mm is generally used, and the preliminarily calcined powder (C) is supported thereon. Its supporting rate is determined taking into account a catalyst use condition, for example, a reaction condition, such as a space velocity of the reaction raw materials, raw material concentrations, or the like, and it is generally 20% by weight to 80% by weight. Here, the supporting rate is expressed according to the following formula (3). There is thus obtained a shaped body (D).

Supporting rate (% by weight)=100×[(Weight of preliminarily calcined powder (C) used for shaping)/{(Weight of preliminarily calcined powder (C) used for shaping)+(Weight of inert carrier used for shaping)+(Weight of shaping auxiliary agent and strength improver used for shaping)}]   Formula (3)

Step e): Full-Scale Calcination

By calcining the shaped body (D) at a temperature of 200 to 600° C. for about 1 to 12 hours, its catalytic activity and effective yield tend to be improved. The calcination temperature is preferably 400° C. or higher and 600° C. or lower, and more preferably 500° C. or higher and 600° C. or lower. Air is simple and easy and preferred as the gas to be circulated; however, besides, it is also possible to use nitrogen or carbon dioxide as an inert gas, or a nitrogen oxide-containing gas, an ammonia-containing gas, a hydrogen gas, or a mixture thereof for the purpose of rendering the system into a reducing atmosphere. There is thus obtained a catalyst (E). By increasing the calcination temperature, the activity can be properly suppressed. Such a catalyst can be, for example, used on the side of a raw material gas inlet where a hot spot is generated.

The mechanical strength of the catalyst (E) is also largely influenced by the atomic ratio of the catalyst formulation. That is, the mechanical strength of the catalyst (E) is influenced by the kind of a compound to be formed by regulating the atomic ratios, or the matter that even in the same compound, the phase form of a crystal structure is different. In addition, the diameter of the complex metal oxide particle formed in the preparation step or drying step or the geometric structure of the particle, and the coagulation form thereof change, and therefore, the mechanical strength of the catalyst (E) is also influenced by changes in micro physical properties, such as strength of the compound crystal in the complex metal oxide, or macro physical properties, for example, the particle size distribution of the preliminarily calcined powder. Overall physical properties including not only the preparation method of each step but also the influence of the atomic ratios determine the mechanical strength of the ultimately prepared catalyst. An attrition resistance that is an index expressing the mechanical strength was calculated by using data measured by an attrition resistance tester, tablet, manufactured by Hayashi Rikagaku K.K. In the measurement, the catalyst was rotated at 25 rpm for 10 minutes and then sieved by a standard sieve having a sieve opening of 1.70 mm, and the weight of the catalyst on the sieve was measured, thereby determining the attrition resistance according to the following formula (4). It may be said that the smaller the value of attrition resistance, the more excellent the mechanical strength is. The attrition resistance is preferably 3% by weight or less, more preferably 1.5% by weight or less, and still more preferably 0.5% by weight or less.

$$\text{Attrition resistance (\% by weight)} = 100 \times [\{(\text{Catalyst weight}) - (\text{Catalyst weight remaining on the sieve})\}/(\text{Catalyst weight})] \quad \text{Formula (4)}$$

The catalytic gas-phase oxidation reaction of an alkene using the complex oxide catalyst obtained by the present invention can be carried out by introducing a mixed gas composed of 1 to 10% by volume of an alkene, 5 to 18% by volume of molecular oxygen, 0 to 60% by volume of steam, and 20 to 70% by volume of an inert gas, for example, nitrogen, carbon dioxide, etc., in terms of a raw material gas formulation onto the catalyst prepared above at a temperature ranging from 250 to 450° C. under a pressure of atmospheric pressure to 10 atms for a contact time of 0.5 to 10 seconds. The alkene as referred to in the present invention also includes an alcohol capable of producing an alkene in its intramolecular dehydration reaction, for example, tertiary butanol.

The catalyst of the present invention can be used for the production of an unsaturated aldehyde and/or an unsaturated carboxylic acid. Specifically, the catalyst of the present invention can be used for a method of producing acrolein and acrylic acid by subjecting propylene to gas-phase catalytic oxidation with molecular oxygen or a molecular oxygen-containing gas; and a method of producing methacrolein and methacrylic acid by subjecting isobutylene and/or tertiary butyl alcohol to gas-phase catalytic oxidation with molecular oxygen or a molecular oxygen-containing gas. Above all, it is preferred to use the catalyst of the present invention for the production of acrolein and acrylic acid.

EXAMPLES

Examples are hereunder described by reference to specific examples, but it should be construed that the present invention is not limited to these Examples so long as the gist of the present invention is not deviated.

Example 1

800 parts by weight of ammonium heptamolybdate was completely dissolved in 3,040 parts by weight of pure water (in a weight of 7.0 times the weight of molybdenum) warmed at 60° C. Subsequently, 1.9 parts by weight of potassium nitrate was dissolved in 20 mL of pure water and added to the above-described solution. Subsequently, 305.1 parts by weight of ferric nitrate, 714.4 parts by weight of cobalt nitrate, and 329.4 parts by weight of nickel nitrate were dissolved in 715 mL of pure water warmed at 60° C. These solutions were gradually mixed while stirring. Thereafter, a solution prepared by adding 183.2 parts by weight of bismuth nitrate to a nitric acid aqueous solution (in a weight of 3.0 times the weight of bismuth in bismuth nitrate to be dissolved) which had been prepared by adding 46.6 parts by weight of nitric acid (60% by weight) to 194 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined such that the temperature after 12 hours was 440° C. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 520° C., thereby obtaining Spherical Catalyst 1 having an average particle diameter of 5.2 mm according to the present invention. The catalyst calculated from the charged raw materials was found to be a complex metal oxide having the following atomic ratios.

d/a=3.0, d/g=60, a/g=20
Mo:Bi:Fe:Co:Ni:K=12:1.0:2.0:6.5:3.0:0.050

An attrition resistance of the Catalyst 1 was 0.36% by weight.

Example 2

Spherical Catalyst 2 was obtained in the same manner as that in Example 1, except that the calcination temperature was changed to 540° C.

An attrition resistance of the Catalyst 2 was 0.30% by weight.

Example 3

Spherical Catalyst 3 was obtained in the same manner as that in Example 1, except that the calcination temperature was changed to 560° C.

An attrition resistance of the Catalyst 3 was 0.28% by weight.

Example 4

800 parts by weight of ammonium heptamolybdate was completely dissolved in 3,040 parts by weight of pure water warmed at 60° C. Subsequently, 1.9 parts by weight of potassium nitrate was dissolved in 20 mL of pure water and added to the above-described solution. Subsequently, 350.8 parts by weight of ferric nitrate, 703.4 parts by weight of cobalt nitrate, and 219.6 parts by weight of nickel nitrate were dissolved in 675 mL of pure water warmed at 60° C. These solutions were gradually mixed while stirring. Thereafter, a solution prepared by adding 183.2 parts by weight of bismuth nitrate to a nitric acid aqueous solution which had been prepared by adding 46.6 parts by weight of nitric acid (60% by weight) to 194 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined such that the temperature after 12 hours was 440° C. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 520° C., thereby obtaining Spherical Catalyst 4 having an average particle diameter of 5.2 mm according to the present invention. The catalyst calculated from the charged raw materials was found to be a complex metal oxide having the following atomic ratios.

d/a=2.0, d/g=40, a/g=20
Mo:Bi:Fe:Co:Ni:K=12:1.0:2.3:6.4:2.0:0.050

An attrition resistance of the Catalyst 4 was 0.12% by weight.

Example 5

800 parts by weight of ammonium heptamolybdate was completely dissolved in 3,040 parts by weight of pure water warmed at 60° C. Subsequently, 1.1 parts by weight of potassium nitrate was dissolved in 11 mL of pure water and added to the above-described solution. Subsequently, 259.3 parts by weight of ferric nitrate, 769.3 parts by weight of cobalt nitrate, and 219.6 parts by weight of nickel nitrate were dissolved in 662 mL of pure water warmed at 60° C. These solutions were gradually mixed while stirring. Thereafter, a solution prepared by adding 183.2 parts by weight of bismuth nitrate to a nitric acid aqueous solution which had been prepared by adding 46.6 parts by weight of nitric acid (60% by weight) to 194 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined such that the temperature after 12 hours was 440° C. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 540° C., thereby obtaining Spherical Catalyst 5 having an average particle diameter of 5.2 mm according to the present invention. The catalyst calculated from the charged raw materials was found to be a complex metal oxide having the following atomic ratios.

d/a=2.0, d/g=67, a/g=33
Mo:Bi:Fe:Co:Ni:K=12:1.0:1.7:7.0:2.0:0.030

An attrition resistance of the Catalyst 5 was 0.26% by weight.

Example 6

Spherical Catalyst 6 was obtained in the same manner as that in Example 5, except that the calcination temperature was changed to 560° C.

An attrition resistance of the Catalyst 6 was 0.24% by weight.

Comparative Example 1

800 parts by weight of ammonium heptamolybdate was completely dissolved in 3,040 parts by weight of pure water warmed at 60° C. Subsequently, 3.8 parts by weight of potassium nitrate was dissolved in 40 mL of pure water and added to the above-described solution. Subsequently, 266.9 parts by weight of ferric nitrate, 571.5 parts by weight of cobalt nitrate, and 307.4 parts by weight of nickel nitrate were dissolved in 607 mL of pure water warmed at 60° C. These solutions were gradually mixed while stirring. Thereafter, a solution prepared by adding 305.9 parts by weight of bismuth nitrate to a nitric acid aqueous solution which had been prepared by adding 77.9 parts by weight of nitric acid (60% by weight) to 324 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined such that the temperature after 12 hours was 440° C. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 520° C., thereby obtaining Spherical Catalyst 7 having an average particle diameter of 5.2 mm. The catalyst calculated from the charged raw materials was found to be a complex metal oxide having the following atomic ratios.

d/a=1.7, d/g=28, a/g=17
Mo:Bi:Fe:Co:Ni:K=12:1.7:1.7:5.2:2.8:0.10

An attrition resistance of the Catalyst 7 was 0.13% by weight.

Comparative Example 2

800 parts by weight of ammonium heptamolybdate was completely dissolved in 3,040 parts by weight of pure water warmed at 60° C. Subsequently, 1.9 parts by weight of potassium nitrate was dissolved in 20 mL of pure water and added to the above-described solution. Subsequently, 167.8 parts by weight of ferric nitrate, 439.6 parts by weight of cobalt nitrate, and 384.3 parts by weight of nickel nitrate were dissolved in 526 mL of pure water warmed at 60° C. These solutions were gradually mixed while stirring. Thereafter, a solution prepared by adding 366.3 parts by weight of bismuth nitrate to a nitric acid aqueous solution which had been prepared by adding 93.3 parts by weight of nitric acid (60% by weight) to 388 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined such that the temperature after 12 hours was 440° C. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 520° C., thereby obtaining Spherical Catalyst 8 having an average particle diameter of 5.2 mm. The catalyst calculated from the charged raw materials was found to be a complex metal oxide having the following atomic ratios.

$d/a=1.8$, $d/g=70$, $a/g=40$

Mo:Bi:Fe:Co:Ni:K=12:2.0:1.1:4.0:3.5:0.050

An attrition resistance of the Catalyst 8 was 4.14% by weight.

Comparative Example 3

800 parts by weight of ammonium heptamolybdate was completely dissolved in 3,040 parts by weight of pure water warmed at 60° C. Subsequently, 1.9 parts by weight of potassium nitrate was dissolved in 20 mL of pure water and added to the above-described solution. Subsequently, 274.6 parts by weight of ferric nitrate, 538.5 parts by weight of cobalt nitrate, and 373.3 parts by weight of nickel nitrate were dissolved in 629 mL of pure water warmed at 60° C. These solutions were gradually mixed while stirring. Thereafter, a solution prepared by adding 329.7 parts by weight of bismuth nitrate to a nitric acid aqueous solution which had been prepared by adding 84.0 parts by weight of nitric acid (60% by weight) to 350 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined such that the temperature after 12 hours was 440° C. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 520° C., thereby obtaining Spherical Catalyst 9 having an average particle diameter of 5.2 mm. The catalyst calculated from the charged raw materials was found to be a complex metal oxide having the following atomic ratios.

$d/a=1.9$, $d/g=68$, $a/g=36$

Mo:Bi:Fe:Co:Ni:K=12:1.8:1.8:4.9:3.4:0.050

An attrition resistance of the Catalyst 9 was 1.83% by weight.

Comparative Example 4

800 parts by weight of ammonium heptamolybdate was completely dissolved in 3,040 parts by weight of pure water warmed at 60° C. Subsequently, 3.0 parts by weight of potassium nitrate was dissolved in 33 mL of pure water and added to the above-described solution. Subsequently, 457.6 parts by weight of ferric nitrate, 615.5 parts by weight of cobalt nitrate, and 285.5 parts by weight of nickel nitrate were dissolved in 720 mL of pure water warmed at 60° C. These solutions were gradually mixed while stirring. Thereafter, a solution prepared by adding 256.4 parts by weight of bismuth nitrate to a nitric acid aqueous solution which had been prepared by adding 65.3 parts by weight of nitric acid (60% by weight) to 272 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined such that the temperature after 12 hours was 440° C. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 520° C., thereby obtaining Spherical Catalyst 10 having an average particle diameter of 5.2 mm. The catalyst calculated from the charged raw materials was found to be a complex metal oxide having the following atomic ratios.

$d/a=1.9$, $d/g=33$, $a/g=18$

Mo:Bi:Fe:Co:Ni:K=12:1.4:3.0:5.6:2.6:0.080

An attrition resistance of the Catalyst 10 was 0.52% by weight.

Comparative Example 5

800 parts by weight of ammonium heptamolybdate was completely dissolved in 3,040 parts by weight of pure water warmed at 60° C. Subsequently, 2.3 parts by weight of potassium nitrate was dissolved in 24 mL of pure water and added to the above-described solution. Subsequently, 305.1 parts by weight of ferric nitrate, 494.6 parts by weight of cobalt nitrate, and 439.2 parts by weight of nickel nitrate were dissolved in 657 mL of pure water warmed at 60° C. These solutions were gradually mixed while stirring. Thereafter, a solution prepared by adding 238.1 parts by weight of bismuth nitrate to a nitric acid aqueous solution which had been prepared by adding 60.6 parts by weight of nitric acid (60% by weight) to 252 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined such that the temperature after 12 hours was 440° C. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 520° C., thereby obtaining Spherical Catalyst 11 having an average particle diameter of 5.2 mm. The catalyst calculated from the charged raw materials was found to be a complex metal oxide having the following atomic ratios.

$d/a=3.1$, $d/g=67$, $a/g=22$

Mo:Bi:Fe:Co:Ni:K=12:1.3:2.0:4.5:4.0:0.060

An attrition resistance of the Catalyst 11 was 0.45% by weight.

Comparative Example 6

800 parts by weight of ammonium heptamolybdate was completely dissolved in 3,740 parts by weight of pure water (in a weight of 8.6 times the weight of molybdenum) warmed at 60° C. Subsequently, 1.9 parts by weight of potassium nitrate was dissolved in 20 mL of pure water and added to the above-described solution. Subsequently, 305.1 parts by weight of ferric nitrate, 714.4 parts by weight of cobalt nitrate, and 329.4 parts by weight of nickel nitrate were dissolved in 715 mL of pure water warmed at 60° C. These solutions were gradually mixed while stirring. Thereafter, a solution prepared by adding 183.2 parts by weight of bismuth nitrate to a nitric acid aqueous solution (in a weight of 3.0 times the weight of bismuth in bismuth nitrate to be dissolved) which had been prepared by adding 36.0 parts by weight of nitric acid (60% by weight) to 204 mL of pure water, thereby regulating a nitric acid concentration to 9.0% by weight and then completely dissolving was added to the foregoing solution and mixed with stirring. This slurry was dried by a spray drying method, and the resulting dry powder was preliminarily calcined such that the temperature after 12 hours was 440° C. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 520° C., thereby obtaining Spherical Catalyst 12 having an average particle diameter of 5.2 mm. The catalyst calculated from the charged raw materials was found to be a complex metal oxide having the following atomic ratios.
d/a=3.0, d/g=60, a/g=20
Mo:Bi:Fe:Co:Ni:K=12:1.0:2.0:6.5:3.0:0.050
An attrition resistance of the Catalyst 12 was 3.89% by weight.

Comparative Example 7

800 parts by weight of ammonium heptamolybdate was completely dissolved in 3,740 parts by weight of pure water (in a weight of 8.6 times the weight of molybdenum) warmed at 60° C. Subsequently, 1.9 parts by weight of potassium nitrate was dissolved in 20 mL of pure water and added to the above-described solution. Subsequently, 305.1 parts by weight of ferric nitrate, 714.4 parts by weight of cobalt nitrate, and 329.4 parts by weight of nickel nitrate were dissolved in 715 mL of pure water warmed at 60° C. These solutions were gradually mixed while stirring. Thereafter, a solution prepared by adding 183.2 parts by weight of bismuth nitrate to a nitric acid aqueous solution (in a weight of 3.0 times the weight of bismuth in bismuth nitrate to be dissolved) which had been prepared by adding 46.6 parts by weight of nitric acid (60% by weight) to 194 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined such that the temperature after 12 hours was 440° C. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 520° C., thereby obtaining Spherical Catalyst 13 having an average particle diameter of 5.2 mm. The catalyst calculated from the charged raw materials was found to be a complex metal oxide having the following atomic ratios.
d/a=3.0, d/g=60, a/g=20
Mo:Bi:Fe:Co:Ni:K=12:1.0:2.0:6.5:3.0:0.050
An attrition resistance of the Catalyst 13 was 0.33% by weight.

Comparative Example 8

800 parts by weight of ammonium heptamolybdate was completely dissolved in 3,040 parts by weight of pure water (in a weight of 7.0 times the weight of molybdenum) warmed at 60° C. Subsequently, 1.9 parts by weight of potassium nitrate was dissolved in 20 mL of pure water and added to the above-described solution. Subsequently, 305.1 parts by weight of ferric nitrate, 714.4 parts by weight of cobalt nitrate, and 329.4 parts by weight of nickel nitrate were dissolved in 715 mL of pure water warmed at 60° C. These solutions were gradually mixed while stirring. Thereafter, a solution prepared by adding 183.2 parts by weight of bismuth nitrate to a nitric acid aqueous solution (in a weight of 2.2 times the weight of bismuth in bismuth nitrate to be dissolved) which had been prepared by adding 33.5 parts by weight of nitric acid (60% by weight) to 140 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined such that the temperature after 12 hours was 440° C. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 520° C., thereby obtaining Spherical Catalyst 14 having an average particle diameter of 5.2 mm. The catalyst calculated from the charged raw materials was found to be a complex metal oxide having the following atomic ratios.
d/a=3.0, d/g=60, a/g=20
Mo:Bi:Fe:Co:Ni:K=12:1.0:2.0:6.5:3.0:0.050
An attrition resistance of the Catalyst 14 was 0.33% by weight.

Comparative Example 9

800 parts by weight of ammonium heptamolybdate was completely dissolved in 3,040 parts by weight of pure water (in a weight of 7.0 times the weight of molybdenum) warmed at 60° C. Subsequently, 1.9 parts by weight of potassium nitrate was dissolved in 20 mL of pure water and added to the above-described solution. Subsequently, 305.1 parts by weight of ferric nitrate, 714.4 parts by weight of cobalt nitrate, and 329.4 parts by weight of nickel nitrate were dissolved in 715 mL of pure water warmed at 60° C. These solutions were gradually mixed while stirring. Thereafter, a solution prepared by adding 183.2 parts by weight of bismuth nitrate to a nitric acid aqueous solution (in a weight of 3.0 times the weight of bismuth in bismuth nitrate to be dissolved) which had been prepared by adding 36.0 parts by weight of nitric acid (60% by weight) to 204 mL of pure water, thereby regulating a nitric acid concentration to 9.0% by weight and then completely dissolving was added to the foregoing solution and mixed with stirring. This slurry was dried by a spray drying method, and the resulting dry powder was preliminarily calcined such that the temperature after 12 hours was 440° C. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 520° C., thereby obtaining Spherical Catalyst 15 having an average particle diameter of 5.2 mm. The catalyst calculated from the charged raw materials was found to be a complex metal oxide having the following atomic ratios.

d/a=3.0, d/g=60, a/g=20

Mo:Bi:Fe:Co:Ni:K=12:1.0:2.0:6.5:3.0:0.050

An attrition resistance of the Catalyst 15 was 2.41% by weight.

Comparative Example 10

Spherical Catalyst 16 was obtained in the same manner as that in Comparative Example 7, except that the calcination temperature was changed to 540° C.

An attrition resistance of the Catalyst 16 was 0.29% by weight.

Results of an oxidation reaction of propylene are hereunder shown. Here, definitions of propylene conversion, acrolein yield, acrylic acid yield, and effective yield are as follows.

Propylene Conversion (mol %)={(Molar number of reacted propylene)/(Molar number of fed propylene)}×100

Acrolein yield (mol %)={(Molar number of produced acrolein)/(Molar number of fed propylene)}×100

Acrylic acid yield (mol %)={(Molar number of produced acrylic acid)/(Molar number of fed propylene)}×100

Effective yield (mol %)=(Acrolein yield)+(Acrylic acid yield)

The oxidation reaction of propylene was carried out by using the above-prepared Catalysts 1 to 16, thereby determining the propylene conversion, the acrolein yield, the acrylic acid yield, and the effective yield. 68 mL of the catalyst was filled in a stainless steel-made reaction tube having an inside diameter of 28.4 mm, a mixed gas composed of 8% by volume of propylene, 67% by volume of air, and 25% by volume of steam was introduced for a contact time of 4 seconds to carry out the oxidation reaction of propylene. A reaction bath temperature and an effective yield at the time when the propylene conversion became 97.5% were determined and shown in Table 1.

TABLE 1

Reaction results at the time when the propylene conversion was 97.5%

| | d/a | d/g | a/g | Water/Mo | Nitric acid concentration | Nitric acid/Bi | Calcination temperature (° C.) | Reaction bath temperature (° C.) | Effective yield (mol %) | Attrition resistance (% by weight) |
|---|---|---|---|---|---|---|---|---|---|---|
| Example 1 | 3.0 | 60 | 20 | 7.0 | 12 | 3.0 | 520 | 293 | 88.3 | 0.36 |
| Example 2 | 3.0 | 60 | 20 | 7.0 | 12 | 3.0 | 540 | 300 | 89.2 | 0.30 |
| Example 3 | 3.0 | 60 | 20 | 7.0 | 12 | 3.0 | 560 | 332 | 88.7 | 0.28 |
| Example 4 | 2.0 | 40 | 20 | 7.0 | 12 | 3.0 | 520 | 295 | 89.3 | 0.12 |
| Example 5 | 2.0 | 67 | 33 | 7.0 | 12 | 3.0 | 540 | 305 | 89.2 | 0.26 |
| Example 6 | 2.0 | 67 | 33 | 7.0 | 12 | 3.0 | 560 | 330 | 89.7 | 0.24 |
| Comparative Example 1 | 1.7 | 28 | 17 | 7.0 | 12 | 3.0 | 520 | 325 | 88.4 | 0.13 |
| Comparative Example 2 | 1.8 | 70 | 40 | 7.0 | 12 | 3.0 | 520 | 310 | 87.5 | 4.14 |
| Comparative Example 3 | 1.9 | 68 | 36 | 7.0 | 12 | 3.1 | 520 | 301 | 85.4 | 1.82 |
| Comparative Example 4 | 1.9 | 33 | 18 | 7.0 | 12 | 3.1 | 520 | 305 | 76.2 | 0.52 |
| Comparative Example 5 | 3.1 | 67 | 22 | 7.0 | 12 | 3.0 | 520 | 302 | 84.2 | 0.45 |
| Comparative Example 6 | 3.0 | 60 | 20 | 8.6 | 9 | 3.0 | 520 | 284 | 80.7 | 3.89 |
| Comparative Example 7 | 3.0 | 60 | 20 | 8.6 | 12 | 3.0 | 520 | 284 | 84.1 | 0.33 |
| Comparative Example 8 | 3.0 | 60 | 20 | 7.0 | 12 | 2.2 | 520 | 283 | 81.8 | 0.33 |
| Comparative Example 9 | 3.0 | 60 | 20 | 7.0 | 9 | 3.0 | 520 | 284 | 81.0 | 2.41 |
| Comparative Example 10 | 3.0 | 60 | 20 | 8.6 | 12 | 3.0 | 540 | 291 | 85.1 | 0.29 |

While the invention has been described in detail and with reference to specific embodiments thereof, it will be apparent to one skilled in the art that various changes and modifications can be made therein without departing from the spirit and scope thereof.

It is to be noted that the present application is based on a Japanese patent application filed on May 9, 2013 (Japanese Patent Application No. 2013-099647), the entireties of which are incorporated by reference. In addition, all references cited herein are incorporated as a whole.

INDUSTRIAL APPLICABILITY

The catalyst of the present invention is useful for the production of an unsaturated aldehyde and/or an unsaturated carboxylic acid.

The invention claimed is:

1. A catalyst for producing an unsaturated aldehyde and/or an unsaturated carboxylic acid, comprising:
a compound represented by the following formula (1),
the catalyst being prepared by a method in which in a step of preparing the compound represented by the following formula (1), a molybdenum component raw material is composed of only ammonium molybdate, the weight of water for dissolving the ammonium molybdate is 8.5 times or less relative to the weight of molybdenum contained in the ammonium molybdate, and a bismuth component raw material is composed of only bismuth nitrate, the weight of a nitric acid aqueous solution for dissolving the bismuth nitrate is 2.3 times or more relative to the weight of bismuth contained in the bismuth nitrate, and the nitric acid concentration of the nitric acid aqueous solution for dissolving the bismuth nitrate is 10% by weight or more:

$$Mo_{12}Bi_aFe_bCo_cNi_dZ_gO_h \quad \text{Formula (1)}$$

wherein Z is one or more elements selected from the group consisting of potassium (K), rubidium (Rb) and cesium (Cs); a, b, c, d and g represent atomic ratios of the respective components; h is a numerical value determined by degrees of oxidations of the catalyst components; a=0.80 to 2.0, b=1 to 2.5; c=3 to 7; d=2 to 3.5; g=0.01 to 0.10; h is expressed by the numerical value satisfying oxidation states of other elements; d/a is 1.9 or more and 3.2 or less; d/g is 29 or more and 69 or less; and a/g is 18 or more and 35 or less.

2. The catalyst for producing an unsaturated aldehyde and/or an unsaturated carboxylic acid according to claim 1, which is prepared by shaping a preliminarily calcined powder obtained by calcining a dry powder obtained by drying a slurry containing the component of the formula (1), at a temperature of 200° C. or higher and 600° C. or lower and again calcining the preliminarily calcined powder at a temperature of 200° C. or higher and 600° C. or lower.

3. The catalyst for producing an unsaturated aldehyde and/or an unsaturated carboxylic acid according to claim 2, wherein the shaping method of the catalyst is the method of coating a catalytically active component on a spherical carrier, the average particle diameter of the obtained catalyst is 3.0 mm to 10.0 mm, and a portion of the weight of the catalytically active component occupying in the whole of the catalyst is 20 to 80% by weight.

4. A method for producing a catalyst, which is a production method of the catalyst for producing an unsaturated aldehyde and/or an unsaturated carboxylic acid according to claim 1, wherein in a step of preparing the compound represented by the formula (1), the molybdenum component raw material is composed of only ammonium molybdate, the weight of water for dissolving the ammonium molybdate is controlled to 8.5 times or less relative to the weight of molybdenum contained in the ammonium molybdate, and the bismuth component raw material is composed of only bismuth nitrate, the weight of a nitric acid aqueous solution for dissolving the bismuth nitrate is controlled to 2.3 times or more relative to the weight of bismuth contained in the bismuth nitrate, and the nitric acid concentration of the nitric acid aqueous solution for dissolving the bismuth nitrate is controlled to 10% by weight or more.

5. A method for producing an unsaturated aldehyde and/or an unsaturated carboxylic acid comprising subjecting an alkene to gas-phase oxidation with molecular oxygen or a molecular oxygen-containing gas in the presence of the catalyst according to claim 1.

* * * * *